United States Patent
Zambianco et al.

(10) Patent No.: US 11,572,340 B2
(45) Date of Patent: Feb. 7, 2023

(54) UREA PRODUCTION PROCESS AND PRODUCTION PLANT USING CO2 PRODUCTED BY OXY-COMBUSTION

(71) Applicant: SAIPEM S.p.A., San Donato Milanese (IT)

(72) Inventors: Andrea Zambianco, San Donato Milanese (IT); Donato Montrone, San Donato Milanese (IT); Rossella Polizzi, San Donato Milanese (IT); Massimiliano Sala, San Donato Milanese (IT); Gioia Usai, San Donato Milanese (IT)

(73) Assignee: SAIPEM S.P.A., San Donato Milanese (IT)

( * ) Notice: Subject to any disclaimer, the term of this patent is extended or adjusted under 35 U.S.C. 154(b) by 232 days.

(21) Appl. No.: 16/635,099

(22) PCT Filed: Aug. 3, 2018

(86) PCT No.: PCT/IB2018/055861
§ 371 (c)(1),
(2) Date: Jan. 29, 2020

(87) PCT Pub. No.: WO2019/026044
PCT Pub. Date: Feb. 7, 2019

(65) Prior Publication Data
US 2021/0363100 A1    Nov. 25, 2021

(30) Foreign Application Priority Data

Aug. 4, 2017   (IT) .................. 102017000090748

(51) Int. Cl.
*C07C 273/04*       (2006.01)
*C01C 1/04*         (2006.01)
(Continued)

(52) U.S. Cl.
CPC .......... *C07C 273/04* (2013.01); *C01C 1/0488* (2013.01); *C07C 273/10* (2013.01); *C07C 273/16* (2013.01)

(58) Field of Classification Search
None
See application file for complete search history.

(56) References Cited

U.S. PATENT DOCUMENTS

| | | | |
|---|---|---|---|
| 5,523,483 A * | 6/1996 | Singh ................ | C07C 273/10 564/68 |
| 2003/0098149 A1 | 5/2003 | Wellington et al. | |
| 2015/0183650 A1 | 7/2015 | Younes et al. | |

FOREIGN PATENT DOCUMENTS

| | | |
|---|---|---|
| CN | 103615713 | 3/2014 |
| EA | 201170573 A1 | 10/2011 |

(Continued)

OTHER PUBLICATIONS

Russian Office Action and Search Report for Application No. 2020109372/04(015349) dated Sep. 30, 2021 (6 pages).

(Continued)

*Primary Examiner* — Amy C Bonaparte
(74) *Attorney, Agent, or Firm* — Neal, Gerber & Eisenberg LLP

(57) ABSTRACT

A urea production process comprises a step of synthesis of urea by reaction of ammonia and carbon dioxide, where at least part of the carbon dioxide for the urea reaction synthesis is produced in an oxy-combustion process; the oxy-combustion process is specifically a flameless oxy-combustion process.

26 Claims, 2 Drawing Sheets

(51) Int. Cl.
*C07C 273/10* (2006.01)
*C07C 273/16* (2006.01)

(56) References Cited

FOREIGN PATENT DOCUMENTS

| JP | 2017-504778 | 9/2017 |
|---|---|---|
| RU | 2569306 C1 | 11/2015 |
| WO | WO 2009071230 | 6/2009 |
| WO | WO 2009071238 | 6/2009 |
| WO | WO 2009071239 | 6/2009 |
| WO | WO 2014016235 | 1/2014 |
| WO | WO 2014016237 | 1/2014 |
| WO | WO 2015097001 | 7/2015 |
| WO | WO 2015102787 | 7/2015 |

OTHER PUBLICATIONS

Notification Concerning Submission, Obtention or Transmittal of Priority Document for International Application No. PCT/IB2018/055861 dated Oct. 12, 2018.
International Search Report and Written Opinion for International Application No. PCT/IB2018/055861 dated Nov. 22, 2018.
PCT Demand for International Preliminary Examination and Reply to International Search Report and the associated Written Opinion for International Application No. PCT/IB2018/055861 dated Jun. 3, 2019.
Notification of Receipt of Demand by Competent International Preliminary Examining Authority (Form PCT/IPEA/402) for International Application No. PCT/IB2018/055861 dated Jun. 7, 2019.
Notification of Transmittal of the International Preliminary Report on Patentability (Form PCT/IPEA/416) for International Application No. PCT/IB2018/055861 dated Jul. 10, 2019.
Joachim Von Scheele et al.: "Flameless oxyfuel combustion for increased production ans reduced C02 and NOx emissions", Warme une Energia, vol. 128, Jan. 1, 2008, pp. 35-40, XP055454504, Retrieved from the Internet: URL:http://www.lindegaspr.com/internet.lg.lg.pri/en/images/Flameless%20oxyfuel%20for%20more%20production%20C02%20NOx%20SuE%200708811_10828.pdf, retrieved on Feb. 27, 2018.
Massimo Malavasi et al.: "Flameless Pressurized Oxy-coal", Apr. 26, 2016, pp. 1-19, XP055454215, Retrieved from the Internet: URL:https://web.archive.org/web/*/http://conference.co2geonet.com/media/1063/european-north-american-10_malavasi.pdf, retrieved on Feb. 26, 2018.
Chinese Office Action and Search Report for Application No. 201880050649.0 dated Dec. 17, 2021 (8 pages).
富氧技术在冶金和煤化工中的应用 Zhao Junxue et al., pp. 124-126, 2013.
Japanese Office Action with translation for Application No. 2020-504239 dated May 25, 2022 (10 pages).

* cited by examiner

UREA PRODUCTION PROCESS AND PRODUCTION PLANT USING CO2 PRODUCTED BY OXY-COMBUSTION

PRIORITY CLAIM

This application is a national stage application of PCT/IB2018/055861, filed on Aug. 3, 2018, which claims the benefit of and priority to Italian Patent Application No. 102017000090748, filed on Aug. 4, 2017, the entire contents of which are each incorporated by reference herein.

TECHNICAL FIELD

This disclosure relates to a urea production process and production plant using CO2 produced by oxy-combustion of a carbon supply.

The requirements of environmental protection are increasingly felt and require inter alia a relatively careful monitoring of CO2 emissions.

Therefore, in various industrial sectors the adoption of solutions characterized by relatively high energy efficiency and by the reduction in the emission of pollutants and of CO2 is sought, for example through the recycling of the latter.

BACKGROUND

In the industrial urea production complexes, that normally include an ammonia plant and a urea plant, the carbon dioxide ("CO2") required for urea synthesis is recovered in the ammonia plant (via process gas cleaning with certain known technologies) and is sent to the urea plant. The quantity of CO2 recoverable from the ammonia plant is a function of the capacity of the plant itself (in terms of produced ammonia) and of the supply composition. Especially in cases of supply with a relatively high methane content gas (i.e., so-called "light" fuels) the quantity of produced CO2 can prove to be relatively limiting, with respect to the available ammonia, for the capacity of the urea plant. In these cases, the solutions adopted to increase the quantity of available CO2 are:

1. enlargement of the ammonia plant's process gas production section (i.e., the section configured to produce hydrogen starting from fossil fuel);
2. the capture of CO2 from the exhausts of the reforming oven and/or from other chimneys (e.g., gas turbines, auxiliary boilers, etc.) typically following washing with amine (or with another solvent) and subsequent regeneration. The separation occurs by physical-chemical absorption of CO2, that in order to be used has to be compressed at suitable pressures for the urea synthesis reaction.

However, it should be appreciated that these solutions may cause further problems themselves.

In particular, in the case of ammonia plants based on reforming or gasification, the enlargement of the ammonia plant's process gas production section to increase the production of CO2 entails a corresponding increase of energy consumption. Instead, in case of CO2 recovery from chimneys, the costs to be borne for the installation of a new unit and the operating costs for the regeneration and the reintegration of the solvent have to be considered.

On the other hand, with ammonia plants that are based on reforming or gasification of hydrocarbons (for example in case H2 and N2 are available from other sources external to the plants) it is not possible to convert the produced ammonia in urea due to the lack of CO2 that should be made available from other sources.

A known technology for the production of CO2 is based on oxy-combustion processes.

Briefly, oxy-combustion is a kind of combustion in which a fuel is burnt using oxygen as a primary oxidant instead of air.

In general, since air's nitrogen is not present, the concentration of CO2 in the oxy-combustion's discharged exhausts increases. The oxy-combustion mainly produces water vapor and concentrated carbon dioxide, relatively simplifying the separation of CO2 and/or its recycling. The discharged exhausts have a significantly lower nitrogen content compared with what can be obtained with the traditional combustion processes (and therefore also a definitely lower content of nitrogen oxides that are instead normally produced in the traditional air combustion processes and constitute particularly dangerous pollutants) and mostly contain CO2 and water vapor. Therefore, by cooling the discharged gases to condense the water, CO2 is recovered with relative minimal energy consumption. Moreover, the absence of nitrogen in the combustion process results in an improvement of the energy efficiency of the system since the heating of inert materials is avoided.

An example of the application of oxy-combustion for the recovery of CO2 in industrial ammonia and urea production processes/plants is described in U.S. Patent Application Publication No. 2015/0183650.

In particular, U.S. Patent Application Publication No. 2015/0183650 describes the integration of an ammonia synthesis section with a standard oxy-combustion system. Such an ammonia synthesis section comprises an ammonia synthesis unit, where crude ammonia is produced starting from hydrogen and nitrogen; and a separation unit where the raw ammonia is condensed and separated from the unreacted nitrogen and hydrogen to produce a flow of purified ammonia. An oxy-combustion reactor, where the combustion of a fuel in the presence of oxygen coming from an air separation unit takes place, is used to generate hot water or steam, to be thermally integrated with the ammonia plant, in particular by thermal connection lines that connect the oxy-combustion reactor to the ammonia synthesis unit, and/or the air separation unit with the ammonia separation unit.

The integrated plant described in U.S. Patent Application Publication No. 2015/0183650 produces ammonia (using the hydrogen available from other sources external to the plant and nitrogen obtained from the air separation section) and CO2 captured in the oxy-combustion process. In a specific application the conversion of the products themselves (ammonia and CO2) into urea is also foreseen, in a dedicated urea plant.

In the U.S. Patent Application Publication No. 2015/0183650 solution, the plant for the production of ammonia is necessary both for the purification of the exhausts exiting from the standard oxy-combustion section (with a high NOx and SOx content if the fed supply contains nitrogen and sulphur) and for the subsequent urea synthesis, if present.

The plants and processes of the kind described in U.S. Patent Application Publication No. 2015/0183650, like other similar ones, may however prove to be not entirely satisfactory, at least for some applications.

For example, in the hypothesis described above of a urea production plant in which the CO2 proves to be limiting with respect to the available ammonia, the U.S. Patent Application Publication No. 2015/0183650 solution is not applicable for the following reasons:

additional ammonia synthesis and separation sections thermally integrated with the oxy-combustion unit are required. Therefore, it is not possible to produce only the CO2 requested to close the material balance without producing ammonia at the same time;

H2 has to made available from another unit of the plant.

Moreover, the generic oxy-combustion does not enable to feed multiple supplies of whatever nature and can be subject to the typical problems of any burner linked to variations in the fuel flow.

SUMMARY

One of the purposes of this disclosure is that of supplying a urea process and a urea production plant that enable to overcome certain of the highlighted drawbacks of certain of the prior art.

In particular, one of the purposes of the disclosure is that of improving the efficiency of the known urea production processes/plants and to increase their flexibility in terms of kind and flow rate of the supply.

Therefore, in certain embodiments, this disclosure relates to a urea production process including synthesizing urea by a reaction of ammonia and carbon dioxide. In these embodiments, at least part of the carbon dioxide for the synthesis is produced in an oxy-combustion process including a flameless oxy-combustion process.

In certain other embodiments, this disclosure relates to a urea production plant including a urea unit configured to produce urea by a urea reaction synthesis of ammonia and carbon dioxide. The urea production plant of these embodiments also includes an oxy-combustion unit configured to produce carbon dioxide configured to be sent to the urea unit to feed the urea synthesis reaction. The oxy-combustion unit of these embodiments includes a flameless oxy-combustion unit including a flameless combustor configured to perform a flameless oxy-combustion process of a carbon supply.

According to the present disclosure, a part or all the carbon dioxide required for the urea synthesis is produced in an oxy-combustion process of a carbon supply carried out with specific modes: specifically, the oxy-combustion process is a flameless oxy-combustion process, such as pressurized. In this way, the oxy-combustion process and the related oxy-combustion unit in which the oxy-combustion process is carried out are integrated in the urea process/production plant in a much more efficient and beneficial way compared with the prior art, in particular compared with the solution proposed by U.S. Patent Application Publication No. 2015/0183650, allowing to manage the feeding of carbon supplies having a different physical state and a different composition and with variable flows inside the same combustor without having exhausts with a relatively high content of NOx and SOx that require purification.

The oxy-combustion is carried out in a specific reactor, such as pressurized, that can be integrated inside already existing or new urea plants.

The disclosure thereby gains the following advantages:

the capture of CO2 is significantly relatively simplified due to its relative high concentration in the exhausts and the relative low content of contaminants and inert materials;

the wide flexibility of the carbon supply which can be fed enables the use of waste from adjacent plants, otherwise relatively difficult to dispose of and/or to manage;

a surplus of electric energy and/or steam can be exported and/or integrated inside the complex in which one is operating, increasing its efficiency;

by carrying out pressurized flameless oxy-combustion, the pressurized CO2 can be captured, reducing the compression costs for bringing the CO2 to the pressure required by the urea plant;

by carrying out flameless and pressurized oxy-combustion one can considerably reduce the exhaust treatment section, in which, in particular, no washing with ammonia is necessary;

it is possible to reduce (and in some particular cases, depending on the fed supply, even eliminate) the quantity of passivation air possibly required by the urea plant by exploiting the excess oxygen in the combustion exhausts; and it is possible to associate a urea plant with the ammonia plant also when the ammonia is produced with technologies which are different from reforming or gasification of hydrocarbons, for example starting from pure H2 and N2.

In short, the present disclosure enables to increase the capacity of the existing urea production plants, assuring the quantity of required CO2 with respect to the available ammonia.

Moreover, it is possible to use the CO2 produced through the oxy-combustion process/plant in a new urea plant, irrespective of the urea production process and possibly having available ammonia from other sources.

Additional features are described in, and will be apparent from the following Detailed Description and the figures.

BRIEF DESCRIPTION OF THE DRAWINGS

Further characteristics and advantages of the present disclosure will become clear from the description of the following non-limiting embodiments thereof, with reference to the accompanying drawings, in which.

DETAILED DESCRIPTION

Figure 1:
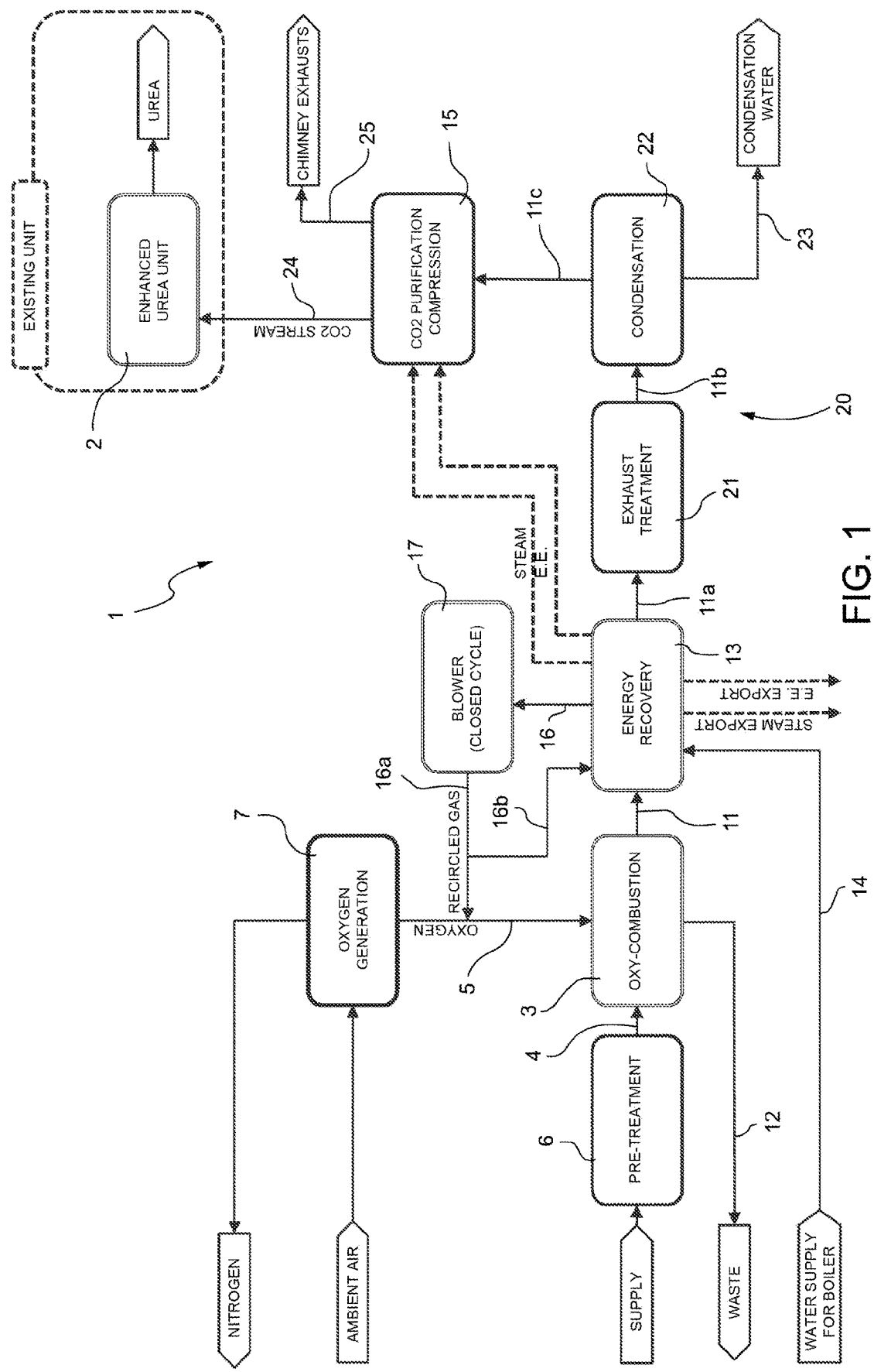
FIG. 1 is a block diagram showing in schematic and simplified form a urea production plant, equipped with an integrated oxy-combustion unit, in accordance with the disclosure.

In FIG. 1 a urea production plant as a whole is indicated with 1 comprising a urea unit 2 configured to produce urea by reaction of ammonia and carbon dioxide, and an oxy-combustion unit 3 in which CO2 is produced to be sent to the urea unit 2 configured to feed the urea synthesis reaction from ammonia and carbon dioxide.

The urea unit 2 (that can also be an existing unit, "enhanced" with the integration of the oxy-combustion unit 3) is not described nor shown in detail for simplicity.

The urea unit 2, as also the urea production process carried out in it, can be of various kinds. For example, but not necessarily, the urea unit 2 can be configured to carry out a traditional so-called "Snamprogetti™ Urea Technology" urea process, but it is understood that the disclosure is also applied to other urea production plants/processes.

In general, the urea unit 2 mainly comprises: a urea synthesis section, where the urea reaction synthesis from ammonia and carbon dioxide takes place; some recovery sections (for example a high pressure recovery section, a medium pressure recovery section and a low pressure recovery section), in which a urea solution produced in the synthesis section gradually concentrates with the removal from it of unreacted ammonia and carbon dioxide and water and recirculation of the recovered components; a vacuum concentration section connected to a section for the treatment of process condensates (essentially water); a finishing/solidification section, comprising for example a granulation unit or a prilling tower.

The urea unit 2 receives CO2 (to be used as reagent in the urea reaction synthesis) produced in the oxy-combustion unit 3.

The oxy-combustion unit 3 is fed, by a fuel supply line 4, with a carbon supply (fuel) and, by an oxygen supply line 5, with an oxygen stream (oxidant).

The supply fed by the oxy-combustion unit 3 can be of any kind and physical state (for example low heating value gas, liquid or solid refinery residues, waste material, biomasses, coal, etc.). If necessary, for example in the case of coal-fired power, the supply can be pre-treated, prior to being fed to the oxy-combustion unit 3, in a pre-treatment unit 6 positioned along the fuel supply line 4.

The oxygen that feeds the oxy-combustion unit 3, is produced in an oxygen generation unit 7, connected to the oxy-combustion unit 3 by the oxygen supply line 5.

The oxygen generation unit 7 is for example an air separation unit configured to separate the air in nitrogen and oxygen.

The separation of the air can be carried out with various technologies, for example by fractional distillation or cryogenic fractionation, membrane separation, adsorption on suitable materials (molecular sieves, zeolites, etc.), in particular by so-called pressure swing absorption techniques (Pressure Swing Adsorption, PSA) or vacuum swing absorption (Vacuum Swing Adsorption, VSA) or with hybrid solutions (Vacuum Pressure Swing Adsorption, VPSA).

It is understood that the oxygen generation unit 7 can be of another kind, for example of the kind operating by electrolysis of aqueous solutions.

Figure 2:
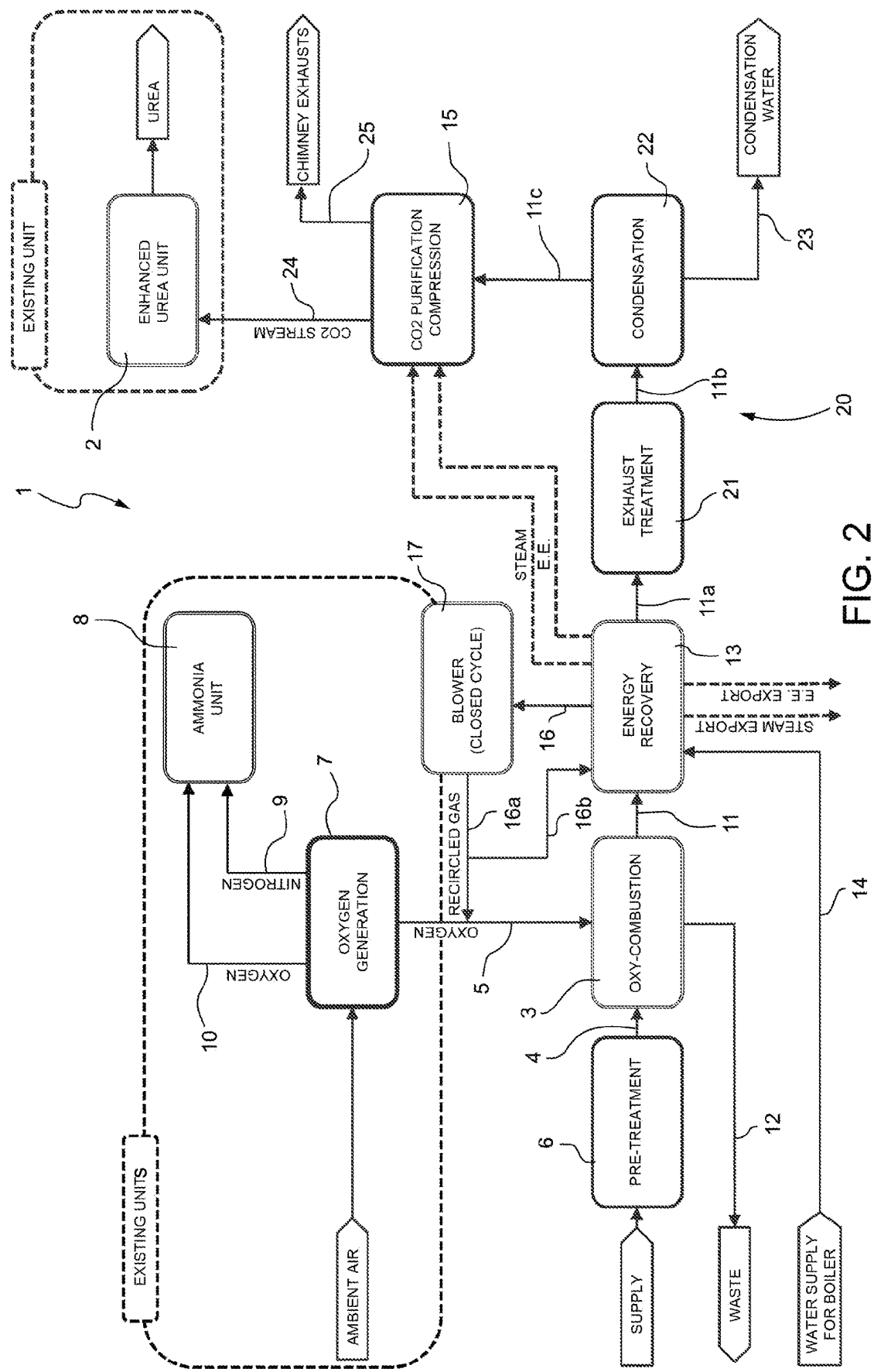
FIG. 2 is a schematic view of a variation of the FIG. 1 plant, also comprising an ammonia unit for the production of ammonia.

Advantageously, as shown in FIG. 2, in the event that the urea production plant 1 includes or is adjacent to an ammonia unit 8 where ammonia is produced and the ammonia unit 8 is based on an autothermal reforming technology (Auto-Thermal Reforming, ATR) that makes use of a cryogenic air separation unit, the oxygen generation unit 7 is an air separation unit defined by said already existing cryogenic air separation unit, with a clear reduction of the investment and operating costs. The oxygen generation unit 7 (that is the air separation unit) is therefore connected, in addition to the oxy-combustion unit 3, also to the ammonia unit 8, by a nitrogen line 9 and an oxygen line 10 that feed nitrogen and oxygen to the ammonia unit 8.

The quantity and purity of the oxygen required by the oxy-combustion unit 3, are in any case such to make the air separation possible also with technologies alternative to cryogenic fractionation, more convenient in terms of investment, as the already mentioned techniques of adsorption or membrane separation that supply oxygen with 90% vol to 95% vol or lower content.

In general, the oxy-combustion unit 3 is fed by an oxygen stream containing at least about 80% vol, and in certain embodiments, at least 90% vol, of oxygen.

The oxy-combustion unit 3 is specifically a flameless oxy-combustion unit, in particular a flameless and pressurized oxy-combustion unit, configured so as to perform a flameless oxy-combustion, in particular a flameless and pressurized oxy-combustion, of the fuel in the presence of oxygen.

In the flameless oxy-combustion process (in certain embodiments, pressurized) carried out in the oxy-combustion unit 3, specifically in a combustor (combustion chamber) of the oxy-combustion unit 3, the carbon supply (fuel) is burnt with the oxygen in such operating conditions that the combustion occurs without generating a flame.

According to the disclosure, the combustor of the oxy-combustion unit 3, is a flameless combustor, in certain embodiments, pressurized and isothermic.

In certain embodiments, the combustor's operating pressure ranges between 0 and 40 bar g.

In certain embodiments, the combustion temperature ranges between about 800° C. and about 1800° C., such as between about 1000° C. and about 1500° C.

As an example, the flameless oxy-combustion process (such as pressurized) is carried out with the modes and in a combustor of the kind described in one or more of the following documents: PCT Patent Application No. WO 2009071230, PCT Patent Application No. WO 2009071238, PCT Patent Application No. WO 2009071239, PCT Patent Application No. WO 2014016235, PCT Patent Application No. WO 2014016237, and PCT Patent Application No. WO 2015097001.

The oxy-combustion process produces exhausts, containing in particular CO2 and that exit from the oxy-combustion unit 3 by an exhaust line 11, and melted waste, that are solidified and inertised and then removed from the oxy-combustion unit 3 through a discharge line 12.

The oxy-combustion unit 3 is connected by the exhaust line 11 to an energy recovery unit 13.

The exhausts produced by the oxy-combustion process, indicatively at temperatures ranging between 1000 and 1500° C., are sent through the exhaust line 11 to the energy recovery unit 13 where the thermal energy is converted into steam and/or electric energy to support the energy consumption of plant 1.

The energy recovery unit 13 is therefore configured so as to recover heat from said exhausts produced in the oxy-combustion unit 3 and produce steam and/or electric energy. For example, the energy recovery unit 13 comprises a boiler fed with water by a water line 14 and that produces steam, which is used as heating fluid to heat other process fluids in plant 1 and/or to generate electric energy by a turbine coupled with a generator.

In particular, steam and/or electric energy generated in the energy recovery unit 13 are used, for example, in a purification and compression unit 15 (described below), that feeds the urea unit 2 with CO2, or in the oxygen generation unit 7.

A possible excess of steam and/or electric energy is integrated with the existing network of plant 1 (thereby improving the overall efficiency of the plant itself), or is exported (that is supplied to users that are external to plant 1).

The steam can be produced in the energy recovery unit 13 at any wanted pressure level (for example by extracting steam from different stages of the steam turbine) so that the steam may be relatively easily integrated with the existing plant. Thus, when the oxy-combustion unit 3 is inserted in a pre-existing urea production plant 1 with the resulting increase in urea production capacity, part of the steam and/or energy produced in the energy recovery unit 13 can be sent to the urea unit 2 to support the greater consumption indeed due to the increase in the production capacity.

Another way to generate electric energy could be for example through a supercritical CO2 cycle instead of a traditional steam cycle.

Part of the exhausts exiting from the energy recovery unit 13 is recirculated, by an exhaust recirculation line 16 fitted with a blower 17, to the oxy-combustion unit 3 and possibly to the energy recovery unit 13.

In particular, the exhaust recirculation line 16 inserts itself in the oxygen supply line 5 with a first arm 16a and is optionally connected, by a second branch 16b, to the energy recovery unit 13.

The remaining part of the exhausts exiting from the energy recovery unit 13 is treated in a CO2 recovery section 20 configured so as to recover (i.e., separate) CO2 from the exhausts with the CO2 purity specification suitable for feeding the urea reaction synthesis carried out in the urea unit 2.

The energy recovery unit 13 is then connected by a portion 11a of the exhaust line 11 to the CO2 recovery section 20. For example, the CO2 recovery section 20 comprises an exhaust treating unit 21, a condensation unit 22, and a purification and compression unit 15, connected to the energy recovery unit 13 and to each other, in series, by respective portions 11a, 11b, 11c of the exhaust line 11.

The exhausts treatment is needed to remove from the exhausts pollutants possibly present in the carbon supply fed by the oxy-combustion unit such as sulphur, chlorine, etc.

The kind of exhausts treatment depends on the composition of the carbon supply fed by the oxy-combustion unit and therefore on the pollutants that are present. For example, if a carbon supply high in sulphur is fed, the exhaust treating unit 21 must be configured to remove the sulphur up to the specification required by the final user and/or by the subsequent treatments; amongst the various possibilities, for example, a lime-based treatment can be carried out. If chlorine is present in the fed supply, a treatment based on caustic soda can be effected, etc.

It should thus be appreciated that the exhaust treating unit 21 can be configured to perform various different treatments; nevertheless, the treatments are in any case relatively simpler and require a relatively lower energy consumption compared with those downstream both in traditional combustion and in generic oxy-combustion.

In one embodiment, an excess of oxygen is present in the exhausts produced by the oxy-combustion process. The excess of oxygen in the exhausts is usefully maintained in the CO2 stream fed to the urea unit 2, since it enables to reduce the quantity of passivation air possibly mixed with CO2 to allow the passivation of the metal surfaces in the urea unit 2, with a further improvement of plant 1's overall efficiency.

The exhausts treated in the exhaust treating unit 21 are then sent to the condensation unit 22, where they undergo condensation for the removal of the water which is present that is removed through a condensates recovery line 23; and then to the purification and compression unit 15, where the CO2 is separated from the exhausts. The CO2 stream separated from the exhausts is fed to the urea unit 2 by a CO2 supply line 24, while the exhausts full of inert materials are discharged, for example to a chimney, by an exhaust discharge line 25.

In one embodiment, the gaseous stream coming from the oxy-combustion unit 3 and from the energy recovery unit 13 via the portion 11a of the exhaust line 11 already has the purity specifications required by the urea unit 2; in this case, usefully, the CO2 recovery section 20 only comprises the condensation unit 22 (since the exhaust treating unit 21 is unnecessary) and a unit 15 reduced to only a compression unit (with no need for purification).

The CO2 exiting from the purification and compression unit 15 is sent to the urea unit 2 and introduced in the most suitable part of the urea unit 2, in certain embodiments, already at the required pressure and possibly mixed with a CO2 stream already available at plant 1.

In one embodiment, the oxy-combustion unit 3 and the subsequent CO2 recovery section 20 supply all the carbon dioxide needed by the urea unit 2. In this case, the CO2 stream exiting from the purification and compression unit 15 is fed directly by the synthesis section of the urea unit 2, at a pressure of about 140 bar to 200 bar and at a temperature of about 90° C. to 150° C.

In other embodiments, the CO2 stream coming from the purification and compression unit 15 is sent instead to the exit (discharge) of a CO2 compressor of the urea unit 2 (at a pressure of about 160 bar g or higher), at the entry (intake) of the same compressor (at a pressure of 0 bar g and 2 bar g) or in one of the intermediate steps (at an intermediate pressure between 2 bar g and 160 bar g).

Finally, it is understood that further modifications and variations can be made to the process and to the plant described hereto that are not outside the scope of the annexed claims. Accordingly, various changes and modifications will be apparent to those skilled in the art and can be made without departing from the spirit and scope of the present subject matter and without diminishing its intended technical scope.

The invention claimed is:

1. A urea production process comprising:
producing, via a flameless oxy-combustion process, carbon dioxide, and
synthesizing urea by a reaction of ammonia and the carbon dioxide, wherein at least part of the carbon dioxide for the synthesis comprises the carbon dioxide produced via the flameless oxy-combustion process.

2. The urea production process of claim 1, wherein the flameless oxy-combustion process comprises a pressurized flameless oxy-combustion process.

3. The urea production process of claim 1, wherein the flameless oxy-combustion process is carried out at a combustion temperature ranging from about 800° C. to about 1800° C.

4. The urea production process of claim 1, wherein the flameless oxy-combustion process is carried out at a pressure ranging from 0 bar g to 40 bar g.

5. The urea production process of claim 1, further comprising feeding the flameless oxy-combustion process with oxygen produced in an oxygen generation process.

6. The urea production process of claim 5, wherein the oxygen generation process comprises an air separation process.

7. The urea production process of claim 1, wherein at least part of the ammonia of the reaction is produced in a synthesis of ammonia by direct reaction of hydrogen and nitrogen, the nitrogen being produced in an air separation process together with oxygen, and a part of the oxygen produced in the air separation process feeds the flameless oxy-combustion process.

8. The urea production process of claim 1, further comprising feeding the flameless oxy-combustion process with an oxygen stream containing at least about 80% vol of oxygen.

9. The urea production process of claim 1, further comprising an energy recovery process including recovering, from an exhaust produced in the flameless oxy-combustion process, thermal energy used to produce at least one of steam and electric energy.

10. The urea production process of claim 9, further comprising recirculating a part of the exhaust to at least one of the flameless oxy-combustion process and the energy recovery process.

11. The urea production process of claim 1, further comprising recovering a carbon dioxide stream from at least a part of an exhaust produced in the flameless oxy-combustion process.

12. The urea production process of claim 11, wherein recovering the carbon dioxide stream comprises:
   treating the exhaust to remove pollutants from the exhaust,
   condensing the exhaust by removing condensate water,
   obtaining the carbon dioxide stream, and
   purifying and compressing the obtained carbon dioxide stream.

13. The urea production process of claim 1, wherein an exhaust produced by the flameless oxy-combustion process contains an excess of oxygen which is maintained in a carbon dioxide stream fed to the reaction and configured to act as a passivation agent.

14. A urea production plant comprising:
   a urea unit configured to produce urea by a urea reaction synthesis of ammonia and carbon dioxide, and
   an oxy-combustion unit configured to produce carbon dioxide which is then sent to the urea unit to feed the urea synthesis reaction, wherein the oxy-combustion unit comprises a flameless oxy-combustion unit comprising a flameless combustor configured to perform a flameless oxy-combustion process of a carbon supply.

15. The urea production plant of claim 14, wherein the oxy-combustion unit comprises a flameless and pressurized oxy-combustion unit and the flameless combustor comprises a pressurized flameless combustor.

16. The urea production plant of claim 14, wherein the flameless combustor is configured to operate at a combustion temperature ranging from about 800° C. to about 1800° C.

17. The urea production plant of claim 14, wherein the flameless combustor is configured to operate at a pressure ranging from 0 bar g to 40 bar g.

18. The urea production plant of claim 14, wherein the oxy-combustion unit is connected to an oxygen generation unit.

19. The urea production plant of claim 18, wherein the oxygen generation unit comprises an air separation unit that is connected to the oxy-combustion unit by an oxygen supply line configured to feed oxygen to the oxy-combustion unit.

20. The urea production plant of claim 18, further comprising an ammonia unit connected to the oxygen generation unit where ammonia is produced by a direct reaction of hydrogen and nitrogen.

21. The urea production plant of claim 20, wherein the oxygen generation unit comprises a cryogenic air separation unit.

22. The urea production plant of claim 14, wherein the oxy-combustion unit is configured to be fed with an oxygen stream containing at least about 80% vol of oxygen.

23. The urea production plant of claim 14, further comprising an energy recovery unit connected to the oxy-combustion unit by an exhaust line configured to convey to the energy recovery unit an exhaust produced in the oxy-combustion unit, wherein the energy recovery unit is configured to recover thermal energy from the exhaust and produce at least one of steam and electric energy.

24. The urea production plant of claim 23, further comprising an exhaust recirculation line that connects the energy recovery unit to at least one of the oxy-combustion unit and the energy recovery unit and is configured to recirculate a part of exhaust to at least one of the oxy-combustion unit and the energy recovery unit.

25. The urea production plant of claim 14, further comprising a carbon dioxide recovery section configured to recover carbon dioxide from at least a part of an exhaust containing carbon dioxide and produced in the oxy-combustion unit.

26. The urea production plant of claim 25, wherein the carbon dioxide recovery section comprises:
   an exhaust treating unit,
   a condensation unit, and
   a purification and compression unit connected to an energy recovery unit,
   wherein the exhaust treating unit, the condensation unit, and the purification and compression unit are connected to each other, in series, by different portions of an exhaust line.

* * * * *